United States Patent
Guilford

(10) Patent No.: US 9,913,801 B2
(45) Date of Patent: *Mar. 13, 2018

(54) TREATMENT OF EVOLVING BACTERIAL RESISTANCE DISEASES INCLUDING KLEBSIELLA PNEUMONIAE WITH LIPOSOMALLY FORMULATED GLUTATHIONE

(71) Applicant: YOUR ENERGY SYSTEMS, LLC, Palo Alto, CA (US)

(72) Inventor: Frederick Timothy Guilford, Palo Alto, CA (US)

(73) Assignee: YOUR ENERGY SYSTEMS, LLC, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/768,007

(22) PCT Filed: Mar. 15, 2013

(86) PCT No.: PCT/US2013/031883
§ 371 (c)(1),
(2) Date: Aug. 14, 2015

(87) PCT Pub. No.: WO2014/126594
PCT Pub. Date: Aug. 21, 2014

(65) Prior Publication Data
US 2015/0374626 A1 Dec. 31, 2015

Related U.S. Application Data

(60) Provisional application No. 61/767,464, filed on Feb. 21, 2013, provisional application No. 61/765,379, filed on Feb. 15, 2013.

(51) Int. Cl.
| | | |
|---|---|---|
| *A61K 31/59* | (2006.01) | |
| *A61K 45/06* | (2006.01) | |
| *A61K 9/127* | (2006.01) | |
| *C12Q 1/18* | (2006.01) | |
| *A61K 31/43* | (2006.01) | |
| *A61K 38/06* | (2006.01) | |
| *A61K 31/407* | (2006.01) | |
| *A61K 9/00* | (2006.01) | |
| *A61K 9/48* | (2006.01) | |
| *C12Q 1/06* | (2006.01) | |

(52) U.S. Cl.
CPC ............ *A61K 9/127* (2013.01); *A61K 9/0095* (2013.01); *A61K 9/4858* (2013.01); *A61K 31/407* (2013.01); *A61K 31/43* (2013.01); *A61K 31/59* (2013.01); *A61K 38/063* (2013.01); *A61K 45/06* (2013.01); *C12Q 1/06* (2013.01); *C12Q 1/18* (2013.01); *G01N 2800/52* (2013.01)

(58) Field of Classification Search
CPC .............. A61K 2300/00; A61K 9/0075; A61K 9/0078; A61K 9/08; A61K 31/5383; A61K 47/02; A61K 9/0073; A61K 31/59; A61K 38/063; A61K 31/407; A61K 31/43; A61K 31/592; A61K 31/593; A61K 9/0095; A61K 9/127; A61K 31/00; A61K 31/198; A61K 31/496; A61K 31/65; A61K 31/711; A61K 45/06; A61K 9/1271; A61K 9/1272; A61K 9/4858
See application file for complete search history.

(56) References Cited

FOREIGN PATENT DOCUMENTS

WO    WO 2007030492    *   3/2007

OTHER PUBLICATIONS

Paez et al FEMS Microbiol Lett 303 (2010) 101-105.*
Friedman. et al. Nitric Oxide. 2011, vol. 25, pp. 381-386.*
Gould et al Biochem Pharmacol. 2011, vol. 81(2), pp. 187-193.*
Schairer Do et al, "Evaluation of the Antibiotic Properties of Glutathione," J Drugs Dermatology, Nov. 1, 2013, vol. 12, No. 11, pp. 1272-1277 PMID 24196336.
Mehta et al, "Alcoholism causes alveolar macrophage zinc deficiency and immune dysfunction," Am J Respir Crit Care Med. Sep. 15, 2013, vol. 188, No. 6,pp. 716-723. PMID 23805351.
"Q&A Antibiotic Resistance," BBC News Health: www.bbc.com/news/health-21739378 posted prior to Nov. 19, 2015.
Walsh, F, "Antibiotics resistance 'as big a risk as terrorism'—medical chief", BBC News-Health- www.bbc.com/news/health-21737844 posted Mar. 11, 2013.
"Klebsiella Pneumoniae in Healthcare Settings," Centers for Disease Control and Prevention, www.cdc.gov/HAI/organisms/klebsiella/klebsiella.html, downloaded Mar. 31, 2017.
Witschi A, Reddy S, Stofer B, Lauterburg BH, The Systemic Availability of Oral Glutathione, Eur J Clin Pharmacol 43:667-669 (1992) PMID: 1362956.
Levitskaia et al, Aminothiol Receptors for Decorporation of Intravenously Administered 60Co in the Rat, Health Physics, vol. 98(1) No. 4: 53-60 (Health Physics Society 2009) PMID: 19959951.
Zeevalk GD, et al, "Liposomal-glutathione provides maintenance of intracellular glutathione and neuroprotection in mesencephalic neuronal cells," Neurochem Res Oct. 2010; 35(10):1575-87. Epub Jun. 10, 2010, PMID: 20535554.
Morris D. et al, "Unveiling the Mechanisms for Decreased Glutathione in Individuals with HIV+ Infection," 2012 Clinical and Developmental Immunology, Article ID 734125, (Hindawi Publishing Corporation accepted Aug. 2011).

* cited by examiner

*Primary Examiner* — Padmavathi Baskar
(74) *Attorney, Agent, or Firm* — Brooke Schumm, III; Daneker, McIntire, Schumm et al

(57) ABSTRACT

The composition of the invention, liposomal glutathione, has been recently shown to have utility for having an antibiotic like effect on *Klebsiella pneumonia* cultures in vitro, and in vivo as demonstrated by efficacy in reducing by large multiples the presence of cultures of *Klebsiella* in rats in animal tests. Further, because the liposomal glutathione bolsters body defenses as well as appearing to have direct killing action, the propensity to create more and more resistant strains to antibiotic treatment is downgraded.

2 Claims, No Drawings

TREATMENT OF EVOLVING BACTERIAL RESISTANCE DISEASES INCLUDING KLEBSIELLA PNEUMONIAE WITH LIPOSOMALLY FORMULATED GLUTATHIONE

CONTINUATION DATA

Priority is claimed from U.S. Provisional Applications 61/765,379 filed Feb. 15, 2013 and 61/767,474 filed Feb. 21, 2013.

TECHNICAL FIELD (STATEMENT OF INDUSTRIAL APPLICABILITY)

The invention relates to the use of liposomally formulated reduced glutathione to treat anti-biotic resistant diseases having evolving bacterial resistance.

BACKGROUND

*Klebsiella pneumonia* is a growing issue in intensive care units as it is a common bacterial contaminant that has become relatively refractory to current treatment regimes. Additionally, because *Klebsiella* tends to be omnipresent in the body, though well controlled, the intensive care unit of a hospital or medical care facility functions as an incubator for strains of *Klebsiella* that have shown an increasing pattern of producing ever more antibiotic resistant strains of *Klebsiella pneumoniae* in patients. Further those strains appear to have a gene characteristic that enables the transfer of the increased antibiotic resistance to other virulent and more widespread diseases which this invention is also designed to curtail.

More broadly, the invention applies to anti-biotic resistant strains of bacteria selected from the family groups of *Klebsiella, Staphylococcus, Clostridium, Shigella, Pneumonia, Escheria coli, Chlamydia*, and Anthrax, and a parasitic disease Leishmaniasis on the same principle because strains of these diseases also have the ability to evolve their resistance to antibiotic treatment.

SUMMARY OF INVENTION

Technical Problem

The technical problem is finding and enabling a composition to diminish the growth of *Klebsiella pneumonia* cultures in the patient's body, particularly in lung tissue, and both bacterial and viral pneumonia more generally. Further, the technical problem is to use a composition that interrupts the cycle of incubation of ever more resistant strains of *Klebsiella* in patients surviving *Klebsiella* infection. It is also important for any treatment to have markers to determine the efficacy promptly and the inventor Dr. Guilford proposes these in conjunction with using liposomally formulated reduced glutathione to treat pneumonia and in particular pneumonia *Klebsiella*.

Solution to Problem

Based on research at Emory University, and enabled in humans by the co-inventor, the inventors propose administration of liposomally formulated reduced glutathione ("liposomal glutathione" or "liposomal reduced glutathione") according to the specifications below for treatment of *Klebsiella pneumonia*, and pneumonia more generally. The enablements herein would improve response to any form of pneumonia, but will be directed to *P. Klebsiella*, and can be applied by a person skilled in the art in the same way to pneumonia more generally. Proposed biomarkers of efficacy in conjunction with the use of liposomal glutathione to treat *Klebsiella* include reduced glutathione levels in the plasma, bronchoalveolar lavage fluid or lung tissue and reduction from elevated levels of TGF-β. The determinative biomarker is finding *Klebsiella* in the blood indicating sepsis, and/or finding the DNA of *Klebsiella* in the blood or other body fluids and tissues.

Advantageous Effects of Invention

The composition of the invention, liposomal glutathione, has been recently shown to have utility for having an antibiotic like effect on *Klebsiella pneumonia* cultures in vitro, and in vivo as demonstrated by efficacy in reducing by large multiples the presence of colonies of *Klebsiella* in rats in animal tests. Further, because the liposomal glutathione bolsters body defenses as well as appearing to have direct killing action, the propensity arising from surviving *Klebsiella* bacteria to create more and more resistant strains to antibiotic treatment is downgraded. Efficacy of treatment can be determined using the biomarkers.

DESCRIPTION OF EMBODIMENTS

The purpose of the present application is to reference the use of liposomally encapsulated reduced glutathione as method of treating *Klebsiella* and as a means of preventing and reversing the formation of cultures of *Klebsiella*.

More broadly, the invention applies to anti-biotic resistant strains of bacteria selected from the family groups of *Klebsiella, Staphylococcus, Clostridium, Shigella, Pneumonia, Escheria, Chlamydia*, and Anthrax, and a parasitic disease Leishmaniasis on the same principle because strains of these diseases also have the ability to evolve their resistance to antibiotic treatment.

"*Klebsiella pneumonia* is traditionally described as a clinically significant opportunistic bacterial pathogen that can infect immunocompromised individuals who are hospitalized and suffer from underlying diseases. In addition to it being a significant clinical pathogen, *K. pneumoniae* is also a normal component of the upper respiratory and GI-tract microbiota of both humans and mice. [f.n. omitted] Lau, H et al, "Host and microbiota factors that control *Klebsiella pneumoniae* mucosal colonization in mice" Microbes Infect. 2008 October (10) 12-13: 1283-1290 (2008) PMC 2633640.

Research has shown that the use of N-Acetyl Cysteine (NAC), a building block of glutathione can have the effect of reversing the oxidative stress in cells. A lack of adequate glutathione in the defensive immune cells such as macrophages can lead to serious deficits in immune defense against infection as related in the discussion of Venketaraman and Brown studies below. However as explained below, NAC requires the function of the enzymes needed to combine the three amino acids of glutathione as well as energy to formulate intracellular glutathione, which energy is often not available in a cell. The inventor believes a compromise of energy and enzyme function occurs because of oxidative stress induced by infections such as *Klebsiella*. Cysteine, as found in NAC has been the only possible oral method, however inefficient, to increase glutathione though it is not particularly effective and no showing has been made of in vivo application. Non-formulated glutathione itself, as a tripeptide, does not survive passage of the gut to be physiologically effective to individual cells such as in lung tissue. Liposomally encapsulated reduced glutathione, the present invention, has been shown in an unpublished study (Lauver) to raise glutathione levels in tissues after oral ingestion in a rabbit model of ischemia (low oxygen) followed by the return of blood flow and oxygen (i.e., reperfusion) injury.

Research was commissioned at the University of Michigan, as yet unpublished showing the surprising effect of the invention in reversing and controlling oxidative stress in tissues such as that which occurs in individuals with illnesses severe enough to require Intensive Care Unit (ICU) admission (PMID 8989180); individuals in the ICU have been shown to be deficient in glutathione due to compromise of the enzymes responsible for the production of glutathione. No publications reference the use of liposomal reduced glutathione to raise tissue levels of glutathione as documented in Lauver et al, University of Michigan Medical School, "Oral Pretreatment With Liposomal Glutathione Attenuates Reperfusion Injury in Rabbit Isolated Hearts," to be published in the Journal of Cardiovascular Pharmacology (2013), That study shows that contrary to the usual degradation in the gut, the invention, purchased from Your Energy Systems, LLC of Palo Alto, Calif., in the amount of approximately 428.8 mg of GSH administered in 5 ml doses, had the following abstracted result:

"A liposomal preparation of glutathione (lipGSH) capable of oral administration was investigated for its ability to attenuate tissue injury and increase myocardial glutathione levels in an isolated heart model of reperfusion injury. Male, New Zealand white rabbits were assigned randomly among four groups: control and daily oral administration of lipGSH for three, seven or fourteen days. At completion of the dosing regimen, hearts were harvested and perfused in a retrograde manner with the use of a Langendorff apparatus. The hearts were subjected to 30 min of global ischemia followed by 60 min of reperfusion. Hearts from lipGSH-treated rabbits exhibited better recovery of left ventricular contractile function during reperfusion and had attenuated oxidative damage. Furthermore, hearts from lipGSH-treated animals had increased myocardial tissue levels of GSH demonstrating effective absorption of lipGSH."

The invention proposes that based on the Lauver et al unpublished research, the administration of liposomally encapsulated glutathione pursuant to the invention would raise the level of intracellular glutathione by at least 30%, particularly in tissues oxidatively stressed.

Plain, non-formulated glutathione used orally is not an option for this therapy as plain glutathione is not absorbed after oral ingestion in humans. A rat study of the removal of a radio-tagged metal (CO-60) from the liver, performed at Pacific Northwest National Laboratory with oral liposomally encapsulated reduced glutathione confirms this observation. The tissue from the control animals (water) served as the 100% of the toxin remaining in the tissue. The animals receiving:

a. Control (water only) showed 100% of the toxin remained=0% removal
b. Plain glutathione, oral, in water showed 100% of the toxin remained=0% removal.
c. Intravenous glutathione showed 36% of the toxin remaining=64% removal.
d. Liposomal reduced glutathione showed 53% of the toxin remaining=47% removal.

The data from this study is consistent with the observation that liposomally encapsulated glutathione is almost as effective as intravenous glutathione in removing the toxin. The plain glutathione has little if any absorption or efficacy. Levitskaia et al, Aminothiol Receptors for Decorporation of Intravenously Administered $^{60}$Co In The Rat, Health Physics, Vol. 98(1) No. 4: 53-60 (Health Physics Society 2009).

More recently, it has been observed that resistance to antibiotic materials has been increasing. For instance, Carbapenem-Resistant *Klebsiella pneumoniae* (CRKP). is resistant to almost all available antimicrobial agents, Over the past 10 years, a progressive increase in CRKP has been seen worldwide. The Centers for Disease Control have asserted that the proportion of enterobacteriaceae resistant to a powerful class of antibiotics known as carbapenems—often the last resort for severe infections—increased to 4.2% in 2011 from 1.2% a decade earlier. The relative increase for the most worrisome type of organism, *Klebsiella*, was even greater, with 10.4% resistance to treatment compared with 1.6% a decade earlier. Dubbed CRE—for carbapenem-resistant enterobacteriaceae—the germs kill up to half of patients who get bloodstream infections from them.

Carbapenems are a class of β-lactam antibiotics with a broad spectrum of antibacterial activity. Carbapenems have a structure that renders them highly resistant to most β-lactamases.

Carbapenems are one of the antibiotics of last resort for many bacterial infections, such as *Escherichia coli* (*E. coli*) and *Klebsiella pneumoniae*. Recently, alarm has been raised over the spread of drug resistance to carbapenem antibiotics among these coliforms, due to production of the New Delhi metallo-β-lactamase, NDM-1. There are currently no new antibiotics in the pipeline to combat bacteria resistant to carbapenems, and worldwide spread of the resistance gene is considered a potential nightmare scenario. The acuity of the problem and non-obviousness of any current solution is highlighted in a recent BBC News article, Roberts, M, Q&A, Antibiotic Resistance, available only on-line at www[dot]bbc[dot]com/news/health-21737844 posted Mar. 11, 2013. It begins with the alarming observation: "Antibiotic resistance is developing at such a pace that we may soon face a future without cures for infection, England's Chief Medical Officer Professor Dame Sally Davies is warning. Her apocalyptic report likens the threat to that of terrorism."

This invention proposes a method to arrest the growth of antibiotic resistant organisms by instead enhancing the body's immune systems so as to be more fully cooperative and functional with antibiotics, and to ally the development of the self-transformation aspects of bacteria and their selection to more antibiotic resistant varieties. http://www.bbc.co.uk[forwardslash]news/health-21739378.

Oral liposomally encapsulated reduced glutathione that is uniquely designed to be absorbed a) across the mucosa of the nose, mouth, gastrointestinal tract, b) after topical application for transdermal, or c) by intravenous infusion of glutathione with or without liposome encapsulation is prepared under the method and according to the composition described as follows:

Basic Dosing Information

For a typical adult ranging from 55 kg to 90 kg, the dose of oral liposomally encapsulated reduced glutathione is oral liposomally encapsulated reduced glutathione 422 mg (1 teaspoon) (5 ml each) at least twice a day. More preferable is administration of 4 teaspoons (5 ml each) 4 times per day. If tolerated well, a loading dose of another teaspoon (5 ml) after perhaps an hour would be helpful.

In a patient who is intubated for ventilator support, monitoring of the individual's pulmonary function and resistance to mechanical ventilation can be monitored as an indication of need for additional liposomal reduced glutathione. Increased airway resistance occurs during constriction of the small airways due to loss of bronchodilation and worsens the ability to adequately support the lung function of the patient. As the individual's lung tissue level of glutathione improves due to therapy with liposomal reduced glutathione improvement in bronchial diameter known as bronchodilation will allow increased lung function. A similar improvement will be identified due improvement in the local lung tissue inflammation due to increased immune cell function. The improvement in bronchodilation will be observed with both liposomal reduced glutathione and liposomally encapsulated GSNO.

There also can be additional enhancement of the liposomally encapsulated function of killing of *Klebsiella* during infection will be obtained by combining administration of the referenced invention with the administration of arginine either orally or intravenously in doses of 500 to 1000 mg 1 to 4 times a day.

There also can be additional combination with the administration of Vitamin D3 or synthetic analogue of Vitamin D3 or vitamin D2 intravenously, intramuscularly, or orally in doses from 5000 IU to 100,000 IU or higher. This combination allows increased function of the enzyme glutathione reductase to regenerate glutathione that has been "used" as an antioxidant and is then in the form of oxidized glutathione (abbreviated "GSSG") back into reduced glutathione abbreviated GSH.

The Vitamin D(25OH) Range of Levels is 30-100 ng/ml.

Reduced Glutathione (GSH) level in plasma range is reduced glutathione: 3.8-5.5 mmol/L The combination of reduced liposomal glutathione combined with vitamin D is proposed, either synthetic or natural, or sunlight therapy to raise vitamin D to a patient critically ill in an ICU setting and monitored with biomarker testing for Vitamin D(25OH), Glutathione levels in serum should be monitored and additional doses of both liposomal glutathione and plain intravenous glutathione should be administered every 4 hours until the patient's condition or plasma level has returned to normal. Additional monitoring includes measurements of serum Transforming growth factor β (TGF β) as well as monitoring the patient's lung function in terms of airway resistance as an indicator of the constriction of the airways and the ability of the airways to allow the normal flow of oxygen and CO2 flow across the alveolar membranes. This can be done by comparing the level of inspired oxygen with the blood level of oxygen, conventionally known as the "blood gas levels".

Additional benefit for the management of the severely ill patients is provided by the infusion of plain, non-encapsulated reduced glutathione. While research shows that liposomal glutathione has significant advantage (100×) over plain glutathione in terms of absorption into cells with phagocytic function such as macrophages and astrocytes (Zeevalk 2010), the direct application of plain glutathione will be helpful in suppressing the *Klebsiella* and other organisms that may be free floating, that is not inside of the cells of the host. Zeevalk, G et al, "Liposomal glutathione provides maintenance of intracellular glutathione and neuroprotection in mesencephalic neuronal cells," Neurochem Research, 2010: October 35 (10), 1575-1587 Epub Jun. 10, 2010 (PMID 21463600).

Another unpublished study in 2010 by V. Venketaraman at Western University investigated the effect of N-acetyl cysteine (NAC) and liposomally encapsulated glutathione to prevent the replication of intracellular *Mycobacterium tuberculosis* after infecting the cells with the organism. Previous work by Venketaraman has shown that raising glutathione levels with NAC in this cell culture model will limit the growth of *Mycobacterium tuberculosis* (TB). The study shows that both NAC and liposomally encapsulated glutathione were able to limit the growth of the organisms to a level below 1000 colony forming units per milliliter (CFU/ml). NAC at 10 millimolar reduced the CFU/ml to 8,000, while the liposomally encapsulated glutathione at 5 micromolar concentration reduced the CFU/ml to 6,000 CFU/ml. This data demonstrates that liposomally encapsulated glutathione is over 2000 times more potent than NAC in maintaining the function of macrophages undergoing the oxidative stress of an intracellular infection.

An additional unpublished study shows that liposomally encapsulated reduced glutathione formulated per this invention has a significantly increased absorption and function in the macrophages from individuals with HIV that are undergoing infection with M. tb (*Mycobacterium tuberculosis*). The absorption of the liposomally encapsulated glutathione is 1000×'s more efficient than the glutathione precursor N-acetyl cysteine (NAC) in restoring normal glutathione levels and restoring the glutathione related function of slowing the replication of M tb in macrophages taken from individuals with HIV . . . "Glutathione Supplementation Improves Immune Function in HIV+Macrophages," Morris D, Guerra C, Khurasany M, Guilford T, Venketaraman V, (unpublished, Western University of Health Sciences, Pomona, Calif. 91766, USA) ("Morris D").

The surprising and novel finding in the unpublished Morris D et al study of the dramatic absorption of liposomally encapsulated reduced glutathione compared to N-acetyl cysteine ("NAC") explains the ability of this formulated form of liposomally encapsulated reduced glutathione to restore macrophage function back to the M1 function.

"In a previous study we observed elevated levels of TGF-β in both the plasma and macrophage culture supernatants of HIV+ macrophages [42]. This elevated TGF-β will compromise the amount of GCLC present inside the cell; consequently, supplementing the raw materials [such as with NAC] for de novo synthesis in HIV+ individuals who are over expressing TGF-β will not result in the same increased production of reduced GSH that is observed in individuals who are not over expressing TGF-β. In addition, this phenomenon may explain why 1GSH [the liposomally encapsulated reduced glutathione of this invention] at lower concentrations than NAC is more effective at raising the concentration of reduced GSH in HIV+ macrophages than in HIV− macrophages. Supplementing with an 1GSH formulation provides complete GSH molecules to cells, circumventing the enzymatic pathway responsible for GSH production, without the requirement for the cell to construct the tripeptide. This may also explain why treatment with 1GSH seems to raise the ratio of reduced GSH to GSSG at much lower concentrations than NAC, as cells treated with NAC will have to produce new molecules of reduced GSH utilizing their own enzymatic machinery. [emphasis added, citation omitted]." Morris et al at pp. 17-18. (To be published shortly in 2013)

The ability to maintain cell function by raising glutathione directly during an infectious process in the cell is novel and has not been previously reported. The observation that liposomally encapsulated glutathione is 2000 (two-thousand) times more effective in maintaining glutathione and the ability of the cell to limit replication of an intracellular infectious agent such as TB is also novel and previously unreported.

Upon entry to an intensive care unit or other site where acute care is being provided to a severely ill patient, prophylactic doses of intravenous GSH, liposomal GSH in doses of 1,000 to 10,000 grams and vitamin D in doses from 10,000 to 100,000 IU should be administered. Subsequent doses of liposomal glutathione and/or plain glutathione should be administered every 4 hours as discussed above.

Severe illnesses may be precipitated by viral infections such as HIV, influenza or Coronavirus, and present as Severe acute respiratory syndrome (SARS). This situation will require assisted ventilation and during this time a state of immune compromise may develop which leaves the individual susceptible to bacterial infection such as the hospital acquired infection including *Klebsiella*.

For management *Klebsiella* related severe infection or sepsis, it is proposed that there be intravenous infusion of 1 gm. of liposomal reduced glutathione every 4 hours for a total of 6 grams per day. The 6 grams intravenous dosing may be modified into different infusion schedules as determined by the circumstances of the patient. That is, the total of 6 grams total amount may be divided into 1.5 gms. every 6 hours if needed.

In these latter situations, the ability to maintain glutathione as a direct, active agent preventing *Klebsiella* replication will be useful. Additionally, the administration of Vitamin D3 or its synthetic derivatives such as Vitamin D2 may be useful in maintaining the function of the enzyme glucose-6 phosphodiesterase known as G6PD. This enzyme is needed for support of the enzyme glutathione reductase, which regenerates oxidized glutathione (GSSG) to reduced glutathione (GSH).

An additional combination is the simultaneous administration of the referenced liposomal reduced glutathione in combination with antibiotics known to have an effect on non-resistant forms of *Klebsiella* in order to improve the efficacy of the antibiotic. The compromise of bacterial function will cause a decreased function in the bacterial needed to metabolize and remove the antibiotic, causing the *Klebsiella* organism to become susceptible to the antibiotic. The ability of the administration of liposomal reduced glutathione in combination with antibiotic will increase the susceptibility of a range of organisms known to be resistant to antibiotics and will include but not be limited to (1) *Klebsiella pneumoniae*, (2) *Klebsiella ozaenae*, (3) *Klebsiella terrigena*, (4) *Klebsiella rhinoscleromatis*, (5) *Klebsiella oxytoca*, (6) *Klebsiella planticola*, and (7) *Klebsiella ornithinolytica*.

Bacteria such as *Klebsiella* and related bacteria possess the ability to transfer DNA via bacterial conjugation, transduction or transformation, which allows genetic material to spread horizontally through an existing population. This process led to the spread of the gene encoding shiga toxin from *Shigella* to *E. coli* O157:H7, carried by a bacteriophage thereby increasing the virulence and active infectious nature of the agent. Similarly, these organisms such as *Shigella* or *E. coli*, or *Klebsiella* can transfer the genes responsible for providing the metabolic resistance to antibiotics found in antibiotic resistant *Klebsiella*. The administration of liposomally reduced glutathione in combination with currently available antibiotics to resistant strains of bacteria will decrease the resistance of the organism and increase the effectiveness of antibiotic therapy. The implication is that the patient can pass the resistant genes from the relatively rare resistant *Klebsiella* to more widespread organisms such as *Shigella*, or *E. coli* or an often sexually transmitted disease: *Chlamydia*.

By way of example, but not limited to the following examples, the liposomal reduced glutathione can be used alone or in combination with antibiotics for the treatment of antibiotic resistant organisms of the *Klebsiella* genus, *Staphylococcus* genus, and also for the *Escherichia* genus including *coli*, and to diminish the effects of *Shigella* and shigellosis, *Chlamydia*, and treatment of the parasite leishmaniasis. The application of the present invention diminishes replication of the *Klebsiella* organism whether or not it has classical antibiotic resistance or not. In the absence of liposomal glutathione, the partially or completely antibiotic resistant organism can self-replicate freely.

*Klebsiella* is a commensal organism in the gastrointestinal tract, but is normally constrained by mechanisms that are not well understood. Based on unpublished research described herein, by restoring natural glutathione levels using the invention where normal glutathione function is otherwise compromised, the organisms are restrained from replication, and in particular, replication to resistant forms. Commensal organisms that appear to be included in the direct action of this invention include *Klebsiella*, *Staphylococcus* genus, and *Escherichia* genus including *coli*. Other organisms introduced into the body subject to the same phenomenon include *Shigella* and shigellosis, *Chlamydia*, and leishmaniasis. *Staphylococcus* genus species include but are not limited to aureus S. aureus group—S. aureus, S. simiae
S. auricularis group—S. auricularis
S. carnosus group—S. carnosus, S. condimenti, S. massiliensis, S. piscifermentans, S. simulans
S. epidermidis group—S. capitis, S. caprae, S. epidermidis, S. saccharolyticus
S. haemolyticus group—S. devriesei, S. haemolyticus, S. hominis
S. hyicus-intermedius group—S. chromogenes, S. felis, S. delphini, S. hyicus, S. intermedius,
S. lutrae, S. microti, S. muscae, S. pseudintermedius, S. rostri, S. schleiferi
S. lugdunensis group—S. lugdunensis
S. saprophyticus group—S. arlettae, S. cohnii, S. equorum, S. gallinarum, S. kloosii, S. leei,
S. nepalensis, S. saprophyticus, S. succinus, S. xylosus
S. sciuri group—S. fleurettii, S. lentus, S. sciuri, S. stepanovicii, S. vitulinus
S. simulans group—S. simulans
S. warneri group—S. pasteuri, S. warneri The invention has further application for the treatment of methicillin resistant *staphylococcus aureus*, commonly referred to as MRSA. MRSA is term used to refer to *staphylococcus aureus* bacteria resistant to beta lactam antibiotics typically thought of as the penicillins and cephalosporins.

Other indications for which treatment is appropriate by liposomal reduced glutathione or for which administering liposomal reduced glutathione is beneficial include signs of infection that may be bacterial such as high fevers, increased white blood count on blood sample testing, findings consistent with pneumonia on physical examination, severe illness requiring administration to the hospital of intensive care unit for conditions that may be accompanied by infection, the finding of low reduced glutathione on blood testing or similar indication of oxidant stress.

The concentration of the glutathione in the liposomes can be in a range from 3.3% w/w to 9% w/w or higher. The amount of 3.3% w/w is equivalent to a concentration of 123 mM. Deionized water can be used to bring w/w percentages up to 100% w/w in any of the tables or formulations below.

Antibiotics Cooperating with Liposomal Reduced Glutathione

In conjunction with the dosing herein, the following antibiotics may be utilized by a practitioner of the medical arts of ordinary skill The dosages of the antibiotics would be the currently prescribed dose on the package insert approved by the U.S. Food and Drug Administration (referred to as the "recommended course of administration").

These antibiotics would include, but not be limited to:
1. Aminoglycoside=Gentamicin, Tobramycin, Netilmicin, Amikacin, Streptomycin.
2. Cephalosporins=Cefazolin, Cefuroxime, Cefotetan, Ceftriaxone, Ceftazidine.
3. Clindamycin
4. Macrolides=Erythromycin, Clarithromycin, Azithromycin.
5. Metronidazole [0109]
6. Penicillins such as Penicillin, Ampicillin, Nafcillin, Piperacillin. These may be used with or without Aztreonam, Imipenem, or with Beta-lactamase inhibitor including, Ampicillin/sulbactam (Augmentum) or Pipercillin/tazobactam and Beta-lactam=Ceftriaxone, Cefuroxime Quinolones=Ciprofloxacin, Ofloxacin, Gatifloxacin or Trovafloxacin
8. Tetracyclines=Tetracycline, Doxycycline, or Minocycline
9. Trimethoprim-Sulfamethoxazole
10. Vancomycin
11. Chloramphenicol
12. Erythromycin
13. telithromycin a ketolide antibiotic.
14. Ethambutol Myambutol isoniazid pyrazinamide rifabutin
Mycobutin rifampin
Rifadin, Rimactane rifapentine
Priftin Carbapenem antibiotics and amikacin capreomycin
Capastat Sulfate cycloserine
Seromycin ethionamide
Trecator levofloxacin
Levaquin moxifloxacin
Avelox para-aminosalicylic acid
Paser streptomycin.
Dosing Selenium should also be administered 200 mg per day if there is inadequate selenium in a patient.

Liposomally encapsulated reduced glutathione (also referred to as liposomal glutathione or liposomal reduced glutathione or liposome-encapsulated glutathione): The preferred dosing schedule of the invention for the treatment of symptoms related to treatment of *Klebsiella* is 800 mg (2 teaspoons) of the invention to be taken twice a day on an empty stomach (that is do not ingest until 30 minutes after eating solid food) and may administered orally or through a nasogastric tube.

1 teaspoon of the invention of oral liposomally encapsulated reduced glutathione reduced contains approximately 420 mg reduced glutathione ("GSH"), and may contain 423 mg reduced glutathione, and 428 mg reduced glutathione.

A preferred mode sets a suggested dose based on body weight. Recommended amounts are for use in the treatment of *Klebsiella*. For best results it is suggested that the invention be used if there is a finding of *Klebsiella*. These doses may also be used if there is a finding of an elevation of a biomarker of *Klebsiella*. Gently stir liposomally encapsulated reduced glutathione into the liquid of your choice.

DETERMINE INDIVIDUAL DOSE BY BODY WEIGHT:
For Children
Under 30 lbs: ¼-½ teaspoon=100-200 mg GSH
30-60 lbs: ½-1 teaspoon=210-420 mg GSH
60-90 lbs: ¾-1.5 teaspoon=316 mg-630 GSH
90-120 lbs: 1-2 teaspoon=422-844 mg GSH
120-150 lbs: 1½-3 teaspoon=630-1260 mg GSH
Over 150 lbs: 1½-3 teaspoons=630-1260 mg GSH The invention should be used on a continuous basis.

Children—should use a dose of liposomally encapsulated reduced glutathione equivalent to 60 mg/Kg of body weight daily in divided doses.

These doses should be continued for the duration of the duration of the illness and for purposes of maintaining adequate glutathione in tissues before, during and after therapy for *Klebsiella*.

The components of this invention can be administered separately or combined in a single capsule or dose.

DETAILED DESCRIPTION OF THE PREFERRED EMBODIMENTS

The methods of manufacture described in Keller et al U.S. Pat. No. 5,891,465, U.S. Pat. No. 6,610,322, and U.S. Pat. No. 6,726,924 and U.S. provisional application No. 60/597,041 by this inventor are adopted herein and into the modes of this invention and can be applied to the examples without undue experimentation. Liposomal formulations preferred in this invention can be purchased from Biozone, Inc. of Pittsburgh, Calif. Reduced glutathione can be purchased from Sigma-Aldrich of St. Louis, Mo. or from Kyowa Hakko USA, Inc., 767 3$^{rd}$ Ave. No. 9, of New York City, N.Y. 10017 with a Western regional office at 85 Enterprise, Suite 430, Aliso Viejo, Calif. 92656. Liposomally encapsulated reduced glutathione can be purchased from Your Energy Systems, LLC, 555 Bryant St., Suite 305, Palo Alto, Calif. 94301.

Example 1

Liposomal Glutathione Drink or Spray 2500 mg Per Ounce or Form Suitable for Encapsulation or Gel

|  | % w/w |
|---|---|
| Deionized Water | 74.4 |
| Glycerin | 15.00 |
| Lecithin | 1.50 |
| Potassium Sorbate (optional spoilage retardant) | 0.10 |
| Glutathione (reduced) | 8.25 |

A lipid mixture having components lecithin, and glycerin were commingled in a large volume flask and set aside for compounding. Hydroxylated lecithin is the preferred ingredient.

In a separate beaker, a water mixture having water, glycerin, glutathione were mixed and heated to, but not more than, 50.degree. C.

The water mixture was added to the lipid mixture while vigorously mixing with a high speed, high shear homogenizing mixer at 750-1500 rpm for 30 minutes.

The homogenizer was stopped and the solution was placed on a magnetic stirring plate, covered with parafilm and mixed with a magnetic stir bar until cooled to room temperature. Normally, a spoilage retardant such as potassium sorbate or BHT would be added. The solution would be placed in appropriate dispenser for ingestion as a liquid or administration as a spray.

Analysis of the preparation under an optical light microscope with polarized light at 400× magnification confirmed presence of both multilamellar lipid vesicles (MLV) and unilamellar lipid vesicles.

The preferred embodiment includes the variations of the amount of glutathione to create less concentrated amounts of liposomally encapsulated glutathione. The amount of glutathione added to the formulation may range from 3.3% w/w to 8.5% w/w or higher. The methods of manufacture described in Keller et al U.S. Pat. No. 5,891,465, U.S. Pat. No. 6,958,160 and U.S. Pat. No. 7,150,883 and U.S. provisional application No. 60/597,041 are incorporated in this description. Concentrations of liposomally encapsulated glutathione from 3.3% w/w, 4% w/w, 5% w/w, 6% w/w, 7% w/w, 7.5% w/w, 8% w/w, 8.5% w/w or 9% w/w liposomally encapsulated glutathione may be formed and utilized for dosing by decreasing the amounts of glutathione and preplacing the material with an increase in the sterile water concentration.

Example 1a

Liposomally encapsulated reduced glutathione Drink or Spray 2500 mg Per Ounce or Form Suitable for Encapsulation or Gel: In %, according to w/w: Deionized Water 75, Glycerin 15.00, Lecithin 1.50, Extract Potassium Sorbate 0.10, Glutathione 8.5 (reduced)

A lipid mixture having components lecithin, ethyl alcohol and glycerin were commingled in a large volume flask and set aside for compounding. Hydroxylated lecithin is the preferred ingredient.

In a separate beaker, a water mixture having water, glycerin, glutathione were mixed and heated, but not more than, 50.degree. C.

The water mixture was added to the lipid mixture while vigorously mixing with a high speed, high shear homogenizing mixer at 750-1500 rpm for 30 minutes.

The homogenizer was stopped and the solution was placed on a magnetic stirring plate, covered with parafilm and mixed with a magnetic stir bar until cooled to room temperature.

A spoilage retardant such as potassium sorbate or BHT would be added. The solution would be placed in appropriate dispenser for ingestion as a liquid or administration as a spray. Analysis of the preparation under an optical light microscope with polarized light at 400× magnification confirmed presence of both multilamellar lipid vesicles (MLV) and unilamellar lipid vesicles.

The preferred embodiment includes the variations of the amount of glutathione to create less concentrated amounts of liposomally encapsulated glutathione. The amount of glutathione added to the formulation may range from 3.3% w/w to 8.5% w/w or higher. The methods of manufacture described in Keller et al U.S. Pat. No. 5,891,465, U.S. Pat. No. 6,958,160 and U.S. Pat. No. 7,150,883 and U.S. provisional application No. 60/597,041 are incorporated in this description.

Concentrations of liposomally encapsulated glutathione from 3.3% w/w, 4% w/w, 5% w/w, 6% w/w, 7% w/w, 7.5% w/w, 8% w/w, 8.5% w/w or 9% w/w liposomally encapsulated glutathione may be formed and utilized for dosing by decreasing the amounts of glutathione and preplacing the material with an increase in the sterile water concentration.

Example 2

Embodiment two of the invention includes the incorporation of the fluid liposome (such as that prepared in Example 1A) into a gelatin based capsule to improve the stability, provide a convenient dosage form, and assist in sustained release characteristics of the liposome. The present embodiment relates to the use of glutathione in the reduced state encapsulated into liposomes or formulated as a preliposome formulation and then put into a capsule. The capsule can be a soft gel capsule capable of tolerating a certain amount of water, a two-piece capsule capable of tolerating a certain amount of water or a two-piece capsule where the liposomes are preformed then dehydrated.

The liposome-capsule unit containing biologically encapsulated material can be taken in addition to orally, used for topical unit-of-use application, or other routes of application such as intra-ocular, intranasal, rectal, or vaginal.

The composition of examples 1 and 2 may be utilized in the encapsulated embodiment of this invention.

Gelatin capsules have a lower tolerance to water on their interior and exterior. The usual water tolerance for a soft gel capsule is 10% w/w on the interior. The concentration of water in a liposome formulation can range from 60-90% water. An essential component of the present invention is the formulation of a liposome with a relatively small amount of water, in the range of 5-10% w/w. By making the liposome in a low aqueous system, the liposome is able to encapsulate the biologically active material and the exposure of water to the inside lining of the capsule is limited. The concentration of water should not exceed that of the tolerance of the capsule for which it is intended. The preferred capsule for this invention is one that can tolerate water in the 15-20% w/w range.

The methods described by Keller et al, U.S. Pat. No. 6,726,924 are incorporated in this description.

Components are commingled and liposomes are made using the injection method (Lasic, D., Liposomes, Elsevier, 88-90, 1993). When liposome mixture cooled down 0.7 ml was drawn into a 1 ml insulin syringe and injected into the open-end of a soft gelatin capsule then sealed with tweezers. Filling of gel caps on a large scale is best with the rotary die method or others such as the Norton capsule machine.

Example 3

Liposomally Encapsulated S-Nitroso-L-Glutathione (GSNO) Drink or Spray 2500 mg Per Ounce or Form Suitable for Encapsulation or Gel

|  | % w/w |
| --- | --- |
| Deionized Water | 74.4 |
| Glycerin | 15.00 |
| Lecithin | 1.50 |
| Potassium Sorbate (optional spoilage retardant) | 0.10 |
| GSNO | 8.25 |

Another method of *Klebsiella* treatment is the encapsulation of GSNO. GSNO (S-nitroso-L-glutathione) in either the lecithin or the self forming liposomes of the current invention for use as an anti-*Klebsiella* therapy. Liposomal encapsulated GSNO, molecular weight 336.3, is 80 mg/ml of liposomal GSNO and the dosing is ½ teaspoon (2.5 ml), to 4 teaspoons (20 ml) orally twice a day which range includes ½ teaspoon (2.5 ml), 1 teaspoon (5 ml), and ½ teaspoon (2.5 ml), increments up to 4 teaspoons (20 ml) orally twice a day.

A lipid mixture having components lecithin, and glycerin were commingled in a large volume flask and set aside for compounding.

In a separate beaker, a water mixture having water, glycerin, GSNO were mixed and heated to, but not more than, 50.degree. C.

The water mixture was added to the lipid mixture while vigorously mixing with a high speed, high shear homogenizing mixer at 750-1500 rpm for 30 minutes.

The homogenizer was stopped and the solution was placed on a magnetic stirring plate, covered with parafilm and mixed with a magnetic stir bar until cooled to room temperature. Normally, a spoilage retardant such as potassium sorbate or BHT would be added. The solution would be placed in appropriate dispenser for ingestion as a liquid or administration as a spray.

Analysis of the preparation under an optical light microscope with polarized light at 400× magnification confirmed presence of both multilamellar lipid vesicles (MLV) and unilamellar lipid vesicles.

The preferred embodiment includes the variations of the amount of glutathione to create less concentrated amounts of liposomally encapsulated glutathione. The amount of glutathione added to the formulation may range from 3.3% w/w to 8.5% w/w or higher. The methods of manufacture described in Keller et al U.S. Pat. No. 5,891,465 are incorporated into this description or as described before may be used.

Concentrations of GSNO from 3.3% w/w, 4% w/w, 5% w/w, 6% w/w, 7% w/w, 7.5% w/w, 8% w/w, 8.5% w/w or 9% w/w liposomally encapsulated GSNO may be formed and utilized for dosing by decreasing the amounts of glutathione and preplacing the material with an increase in the sterile water concentration.

Example 4

Embodiment number four of the present invention includes the creation of liposome suspension using a self-forming, thermodynamically stable liposomes formed upon the adding of a diacylglycerol-PEG lipid to an aqueous solution when the lipid has appropriate packing parameters and the adding occurs above the melting temperature of the lipid. The method described by Keller et al, U.S. Pat. No. 6,610,322 is incorporated into this description.

Most, if not all, known liposome suspensions are not thermodynamically stable. Instead, the liposomes in known suspensions are kinetically trapped into higher energy states by the energy used in their formation. Energy may be provided as heat, sonication, extrusion, or homogenization. Since every high-energy state tries to lower its free energy, known liposome formulations experience problems with aggregation, fusion, sedimentation and leakage of liposome associated material. A thermodynamically stable liposome formulation which could avoid some of these problems is therefore desirable.

The present embodiment prefers liposome suspensions which are thermodynamically stable at the temperature of formation. The formulation of such suspensions is achieved by employing a composition of lipids having several fundamental properties. First, the lipid composition must have packing parameters which allow the formation of liposomes. Second, as part of the head group, the lipid should include polyethyleneglycol (PEG) or any polymer of similar properties which sterically stabilizes the liposomes in suspension. Third, the lipid must have a melting temperature which allows it to be in liquid form when mixed with an aqueous solution.

By employing lipid compositions having the desired fundamental properties, little or no energy need be added when mixing the lipid and an aqueous solution to form liposomes. When mixed with water, the lipid molecules disperse and self assemble as the system settles into its natural low free energy state. Depending on the lipids used, the lowest free energy state may include small unilamellar vesicle (SUV) liposomes, multilamellar vesicle (MLV) liposomes, or a combination of SUVs and MLVs.

In one aspect, the invention includes a method of preparing liposomes. The method comprises providing an aqueous solution; providing a lipid solution, where the solution has a packing parameter measurement of $P_a$ ($P_a$. references the surface packing parameter) between about 0.84 and 0.88, a $P_v$ ($P_v$ references the volume packing parameter) between about 0.88 and 0.93, (See, D. D. Lasic, Liposomes, From Physics to Applications, Elsevier, p. 51 1993), and where at least one lipid in the solution includes a polyethyleneglycol (PEG) chain; and combining the lipid solution and the aqueous solution. The PEG chain preferably has a molecular weight between about 300 Daltons and 5000 Daltons. Kinetic energy, such as shaking or vortexing, may be provided to the lipid solution and the aqueous solution. The lipid solution may comprise a single lipid. The lipid may comprise dioleolylglycerol-PEG-12, either alone or as one of the lipids in a mixture. The method may further comprise providing an active compound, in this case glutathione (reduced); and combining the active compound with the lipid solution and the aqueous solution.

The low molecular weight in the preferred embodiments more effectively deliver the liposomally encapsulated reduced glutathione in active reduced form as needed and thus result in the surprising effect of the invention. The absorption into cells is a particular advantage of the preferred embodiment of the invention.

Further Examples 6

Formulation for Topical Application of Liposomally Encapsulated Reduced Glutathione A topical cream or lotion containing reduced glutathione in a self-forming liposome sold under the brand name "QuSome" ® by Biozone Laboratories, Inc. of Pittsburgh, Calif. is another preferred embodiment. The Qusome self-forming liposome can be formed containing reduced liposomally encapsulated glutathione in a concentration of 5% reduced glutathione encapsulated in the liposome. Most liposomes use energy provided as heat, sonication, extrusion, or homogenization for their formation, which gives them a high energy state. Some liposome formulations can experience problems with aggregation, fusion, sedimentation and leakage of liposome associated material which this invention seeks to minimize and does minimize. The Qusome is a more thermodynamically stable liposome formulation. The Qusome self-forming liposome is self-forming at room temperature which that the mixing of the lipid and an aqueous lipid containing solution avoids alteration of the contents by heating. The resulting liposome is in a low free energy state so it remains stable and reproducible. The formulation of this embodiment is reviewed in example 3.

The methods of manufacture described in Keller et al U.S. Pat. No. 6,958,160 and U.S. Pat. No. 7,150,883 are incorporated in this description. The most important details of that manufacturing are as follows:

The lipids used to form the lipid vesicles and liposomes in the present formulations can be naturally occurring lipids, synthetically made lipids or lipids that are semisynthetic. Any of the art known lipid or lipid like substances can be used to generate the compositions of the present invention. These include, but are not limited to, lecithin, ceramides, phosphatidylethanolamine, phosphotidylcholine, phosphatidylserine, cardiolipin and the like.

Such lipid components for the preparation of lipid vesicles are well known in the art, for example see U.S. Pat. No. 4,485,954, and "Liposome Technology", 2nd Ed, Vol. I (1993) G. Gregoriadis ed., CRC Press, Boca Raton, Fla.

Lipids with these properties that are particularly preferred in the present formulations include phospholipids, particularly highly purified, unhydrogenated lecithin containing high concentrations of phosphotidylcholine, such as that available under the trade name Phospholipon 90 from American Lecithin, or Nattermann Phospholipid, 33 Turner Road, Danbury, Conn. 06813-1908.

In formulating the liposomes, in one aspect, the invention includes a method of preparing liposomes. The method comprises providing an aqueous solution; providing a lipid solution, where the solution has a $P_a$ between about 0.84 and 0.88, a $P_v$ between about 0.88 and 0.93, and where at least one lipid in the solution includes a polyethyleneglycol (PEG) chain; and combining the lipid solution and the aqueous solution. The PEG chain preferably has a molecular weight between about 300 Daltons and 5000 Daltons. Kinetic energy, such as shaking or vortexing, may be provided to the lipid solution and the aqueous solution. The lipid solution may comprise a single lipid. The lipid may comprise dioleolyglycerol-PEG-12, either alone or as one of the lipids in a mixture. The method may further comprise providing an active compound; and combining the active compound with the lipid solution and the aqueous solution.

In another aspect, the invention includes a liposome suspension. The suspension comprises one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain. The PEG chain preferably has a molecular weight between about 300 Daltons and 5000 Daltons. The suspension may comprise a single lipid. The lipid may comprise dioleoylglycerol-PEG-12. The suspension may further comprise an active compound, which may be selected from the group described above.

In another aspect, the invention includes a composition for combining with an aqueous solution to form a liposome suspension. The composition comprises one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain. The PEG chain preferably has a molecular weight between about 300 Daltons and 5000 Daltons. The composition may comprise a single lipid. The composition may comprise dioleoylglycerol-PEG 12. The composition may further comprise an active compound selected from the group above. The composition may be provided in a sealed container, where the container also contains an inert gas to prevent oxidative degradation.

In another aspect, the invention includes a method of intravenously administering a therapeutic compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain; providing an active compound; providing an aqueous solution; combining the composition, compound and solution to form a liposome suspension; and administering the liposome suspension intravenously. The method may further comprise providing kinetic energy to the liposome suspension. The method may also include providing the composition in a sealed container containing an inert gas. The PEG chain preferably has a molecular weight between about 300 Daltons and 5000 Daltons. The composition may comprise a single lipid. The lipid may comprise dioleoylglycerol-PEG-12. The active compound may be selected from the group above.

In another aspect, the invention includes a method of solubilizing an active compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain; providing the active compound; providing an aqueous solution; and combining the active compound, the lipid and the aqueous solution to form a liposome suspension. The method may further comprise providing kinetic energy to the liposome suspension. The method may include providing the composition in a sealed container containing an inert gas. The PEG chain preferably has a molecular weight between about 300 Daltons and 5000 Daltons. The composition may comprise, a single lipid. The lipid may comprise dioleoylglycerol-PEG-12. The active compound may be selected from the group above.

In another aspect, the invention includes a method of orally administering a therapeutic compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain; providing an active compound; providing an aqueous solution; combining the composition, compound and solution to form a liposome suspension; and administering the liposome suspension orally in the form selected from the group comprising a two piece hard gelatin capsule, a soft gelatin capsule, or drops.

The compositions may be administered topically, interorally, vaginally or rectally.

PEG-12 Glyceryl Dioleate was obtained from Global 7 (New Jersey) for the following formulations. This can be substituted for the lecithin w/w % as needed to accomplish the formulation, or applied as set forth below.

In the following formulations, the "set percentage" w/w % of reduced glutathione is selected from 3.3%, 4%, 5%, 6%, 7%, 7.5%, 8%, 8.5% or 9% or amounts approximately to those percentages.

Example 5A

Spontaneous Liposomes for Intravenously Administering Therapeutic Compounds or for a Spray or Drink A set percentage of reduced glutathione is dissolved in a sufficient amount of the solvent PEG-12 Glyceryl Dioleate, also called dioleoylglycerol-PEG 12, (either referred to as "PEGDO") and gently mixed for about 5 minutes. A sufficient amount of PEGDO should be about 10% w/w. Deionized water is slowly added to the solution. Ingredients other than deionized water, the reduced glutathione and the PEGDO may be added such as preferably 0.1% w/w potassium sorbate and then the final amount of deionized water added is that amount which is necessary to have the percentages add up to 100% w/w. Taste or other flavor-masking ingredients could also be added before the deionized water is brought up to 100% w/w. Although taste ingredients can be added before or after the liposomal encapsulation formulation, the preferable mode is to add flavor or other taste masking ingredients after liposomal encapsulation formulation, and they may be ingredients such as corn syrup, honey, sorbitol, sugar, saccharin, stevia, aspartame, citrus seed extract, natural peppermint oil, menthol, synthetic strawberry flavor, orange flavor, chocolate, or vanilla flavoring in concentrations from about 0.01 to 10% w/w. The inventor has preferably used citrus seed extract.

Example 5B

Spontaneous Liposomes for Intravenously Administered Therapeutic Compound and as a Drug Solubilization Vehicle for Use in Spray or Drink A set percentage of reduced glutathione is mixed with a sufficient amount of PEG-12 Glyceryl Dioleate, also called dioleoylglycerol-PEG 12, (either referred to as "PEGDO") to bring the reduced glutathione into solution by vortexing and sonication for 10 minutes. A sufficient amount of PEGDO should be about 5% w/w. Deionized water is added and gently mixed. Ingredients other than deionized water, the reduced glutathione and the PEGDO may be added such as preferably 0.1% w/w potassium sorbate and then the final amount of deionized water added is that amount which is necessary to have the percentages add up to 100% w/w. Ingredients other than deionized water, the reduced glutathione and the PEGDO may be added such as preferably 0.1% w/w potassium sorbate and then the final amount of deionized water added is that amount which is necessary to have the percentages add up to 100% w/w. Taste ingredients or other flavor masking ingredients could also be added before the deionized water is brought up to 100% w/w. Although taste ingredients can be added before or after the liposomal formulation, the preferable mode is to add flavor or other taste masking ingredients after liposomal formulation, and they may be ingredients such as corn syrup, honey, sorbitol, sugar, saccharin, stevia, aspartame, citrus seed extract, natural peppermint oil, menthol, synthetic strawberry flavor, orange flavor, chocolate, or vanilla flavoring in concentrations from about 0.01 to 10% w/w. The inventor has preferably used citrus seed extract.

The QuSome self-forming liposome uses polyethyleneglycol (PEG) is a steric stabilizer and the resulting liposome is of a moderate size, 150 nm-250 nm. The combination of 150 nm-250 nm size and the PEG component is known to create long circulating liposomes. The size of the QuSome self-forming liposome allows them to be sterile filtered.

The concentration of liposomally encapsulated glutathione in the liposomes resulting from the Qusome formulation is 5% w/w for topical application. It is possible to use the Qusome technology in creating an oral formulation also and the 8.25% glutathione in w/w concentration encapsulated in the liposome may be used in the oral formulation.

EXAMPLES

Example 6

The invention is a method of treatment of *Klebsiella pneumonia*, including direct action against the organism, and a composition for the treatment of *Klebsiella pneumoniae* (referenced as "*Klebsiella*" for short) by the direct action of liposomal reduced glutathione. Liposomal reduced glutathione, particularly that formulated by and sold by Your Energy Systems, LLC of Palo Alto, Calif., would be administered to mammalian patients exhibiting respiratory distress or symptoms or upon receipt of a culture identifying the presence of *Klebsiella*, particularly humans. The preferred dosage for a 70 kg patient would be 4 teaspoons daily in an oral formulation having approximately an 8.25% w/w concentration of reduced glutathione in the liposomal formulation. It could be any concentration above 3.3% w/w within the liposomes normally in increments of 0.5% w/w between 3.3% w/w and 9% w/w or higher. There are approximately 423 mg. of reduced glutathione per teaspoon but maybe 420 or 428 mg per teaspoon. Administration may be oral, by inhalation, mucosal, rectal, or intravenous administration.

The dosing applicable for *Klebsiella* is appropriate for *Staphylococcus* genus, and also for the *Escherichia* genus including *coli*, and to diminish the effects of *Shigella* and *shigellosis, Chlamydia*, and *leishmaniasis*.

Unpublished Experimental Evidence:

The invention is directed to correcting reduced glutathione deficiencies in lung tissue(s). By increasing the concentration of reduced glutathione intracellularly in affected lung tissues, direct killing action of the *Klebsiella* organism occurs as reflected in the experiments recited below.

*Klebsiella pneumoniae* were grown overnight in Tryptic Soy Broth (99 ml of broth and 1 ml of bacteria). The broth containing the *K. pneumoniae* was divided into equal volumes, centrifuged, and the pellets were washed twice with phosphate buffered saline (PBS). After the final wash, the two pellets were resuspended, pooled, and brought to a final volume of 10 ml. The final concentration of *K. pneumonia* was ~2×10$^{10}$ colony forming units per ml. After diluting this stock to 2×10$^3$ and 2×10$^2$ colony forming units per ml, 100 μl of these two dilutions were plated onto 100 mm MacConkey Agar Plates. The plates were then misted with 250 μl of liposomal glutathione (182 μl in 100 ml of PBS; Your Energy Systems, LLC, Palo Alto, Calif.) or PBS. After the plates were incubated upside down overnight at 37° C., the number of colony forming units was determined. For the plates misted with PBS, the colony forming units were 200 and 20 for the 2×10$^3$ and 2×10$^2$ dilutions, respectively. For the plates misted with liposomal glutathione, the colony forming units were 5 and 1 for the 2×10$^3$ and 2×10$^2$ dilutions, respectively.

Using a standard protocol [Yeligar et al., J. Immunol. 188(8):3648-57 (2012)], control and ethanol-fed male C57BL/6J mice (aged 8-10 weeks; Jackson Laboratory, Bar Harbor, Me.) were given an intra-tracheal inoculation of *K. pneumoniae* (2×10$^6$ colony forming units; 100 μl). At the four hour time point, mice were randomized to treatment with an oral dose of PBS (20 μl) or liposomal glutathione (20 μl of 84.5 mg/ml). At the 20 hour time point, the colony forming units in the lung were determined. For the control mice, the colony forming units of *K. pneumoniae* in the lung fluid were 40±3 and 21±4 in the PBS and liposomal glutathione treated groups, respectively. For the ethanol-fed mice, the colony forming units of *K. pneumoniae* were 62±8 and 16±5 in the PBS and liposomal treated groups, respectively. In some studies, mice were randomized to an intranasal treatment of 25 µl per nasal nare of PBS or liposomal glutathione (182 µl in 100 ml of PBS) at the four hour time point. For the control mice, the colony forming units of *K. pneumoniae* in the lung fluid were 42±5 and 19±6 in the PBS and liposomal glutathione treated groups, respectively. For the ethanol-fed mice, the colony forming units of *K. pneumoniae* were 74±9 and 14±6 in the PBS and liposomal treated groups, respectively.

Example 7

Markers for *Klebsiella*

Among other markers, a marker for showing *Klebsiella* in lung tissue and to be combined with the novel method of treatment is to examine reduced glutathione levels in the plasma, bronchoalveolar lavage (BAL) fluid or lung tissue. The inventors propose to initially measure the glutathione levels which normally contains 350-500 micromole (µM) GSH in the lavage fluid or lung tissue, correlate that to existing *Klebsiella* culture, and then examine the glutathione level progression in the lavage or lung tissue in subsequent BAL glutathione determinations to determine the efficacy and dosage of the liposomal glutathione proposed to be used to treat the *Klebsiella*.

Another marker for administration of the present invention is to administer liposomally formulated reduced glutathione to individuals with elevations of the cytokine known as transforming growth factor β or transforming growth factor β1 in a blood sample. Transforming growth factor β (TGF-β), which is used to denote both Transforming growth factor β and Transforming growth factor β1, is the most potent and ubiquitous profibrogenic cytokine and its expression is increased in almost all fibrotic diseases. Examples of fibrotic diseases include the fibrosis found in chronic lung diseases described as pulmonary fibrosis, which are associated with chronic lung infection and inflammation. Studies have shown that TGF-β1 decreases intracellular GSH concentration in various types of cells in vitro. Elevated TGF-β can decrease the level of GSH by inhibiting the production and enhance degradation of GCLC, the catalytic subunit of the enzyme responsible for the rate-limiting step in de novo synthesis of reduced glutathione (rGSH). This means that in situations with elevations of TGF-β1 that the building blocks of GSH (such as cysteine found in N-acetyl cysteine, abbreviated NAC) are not as effective as supplying the whole molecule of GSH as is supplied by liposomal reduced glutathione. It has been shown that that liposomal reduced glutathione is 1000 times more effective than NAC in supporting macrophage cell function in the presence of elevated TGF-β1 (Morris 2013). The expected value of measure for TGF-β would be: Normal human subjects were 4.1+/−2.0 ng/ml TGF-beta1 (range, 2.0-12.0 in plasma (1) (2) with >137+/−81 ng/mL in serum considered abnormal (3). A patient responding appropriately to the treatment with liposomally formulated reduced glutathione would begin to diminish from elevated levels back to normal levels.

Thus an aspect of the invention is a method of treatment of *Klebsiella pneumoniae* with liposomally formulated reduced glutathione in a mammalian patient according to the dosages given above.

Another aspect of the invention is a composition of liposomally formulated glutathione formulated as set forth herein for treatment of *Klebsiella pneumoniae* in a mammalian patient according to the dosages given above.

No claim of sole inventorship is made as to these two latter aspects by Dr. Frederick Timothy Guilford.

Another aspect of the invention is a method of treatment of viral or bacterial pneumonia more generally with liposomally formulated reduced glutathione in a mammalian patient according to the dosages given above.

Another aspect of the invention is a composition of Liposomally encapsulated S-Nitroso-L-glutathione (GSNO) Drink or Spray for treatment of *Klebsiella pneumoniae* and other infectious diseases such as *staphylococcus, E. coli, Chlamydia*, and *leishmaniasis* referenced in this invention.

Another aspect of the invention is the addition of Vitamin D with liposomal formulated reduced glutathione for treatment of *Klebsiella pneumoniae* and other infectious diseases such as *staphylococcus, E. coli, Chlamydia*, and *leishmaniasis* referenced in this invention.

Another aspect of the invention is a composition of liposomally formulated glutathione formulated as set forth herein for treatment of bacterial and viral pneumonia in a mammalian patient.

Another aspect of the invention is a composition of liposomally formulated glutathione formulated as set forth herein for treatment of a *staphylococcus* infection in a mammalian patient.

Another aspect of the invention is a composition of liposomally formulated glutathione formulated as set forth herein for treatment of a *Chlamydia* infection in a mammalian patient.

Another aspect of the invention is a composition of liposomally formulated glutathione formulated as set forth herein for treatment of a leishmaniasis parasite in a mammalian patient.

Another aspect of the invention is a composition of liposomally formulated glutathione formulated as set forth herein for treatment of anthrax infection in a mammalian patient.

Another aspect of the invention is a composition of liposomally formulated glutathione formulated as set forth herein for treatment of an *Escheria*, including *E. Coli* infection in a mammalian patient.

Another aspect is evaluating according to the invention biomarkers in association with the compositions, compositions for treatment and methods of treatment in order to assess the effectiveness in a patient of the proposed treatment. Key biomarkers to measure to show effectiveness of the compositions for treatment and methods of treatment are: reduction of elevated TGF-β, examining glutathione levels which are likely deficient and examining the progress of these levels to normal levels in plasma, bronchoalveolar lavage fluid or lung tissue.

I claim:

1. A method of measuring the effectiveness of treatment of a patient using liposomal reduced glutathione in combination with an antibiotic against an antibiotic-resistant bacteria normally treated by said antibiotic, comprising the following steps:
   initially measuring TGF-β in the blood plasma of a patient;
   if TGF-beta is above a normal level administering, to a patient having disease symptoms arising from antibiotic resistant strains of bacteria of *Klebsiella pneumoniae*, intravenously and thereafter if patient compliance can be assured, orally, a dose of a reduced glutathione stabilized and encapsulated in a liposomal pharmaceutical carrier capable of being ingested orally, and capable of delivering glutathione (reduced) in a physiologically active state to improve symptoms in disease states by transfer of the glutathione into animal cells, where the concentration of reduced glutathione in the entrapped aqueous space of the liposomes is at least 123 mM;

simultaneously administering the course of antibiotic through the recommended course of administration of said antibiotic;

measuring the reduction of elevated TGF-β in blood plasma;

measuring whether the level of said bacteria has fallen; and thereafter continuing to administer said glutathione and re-measuring said level of said bacterial until normal bodily health is achieved.

2. The method according to claim 1, further comprising the following step:

administering Vitamin D.

* * * * *